Figure 2:
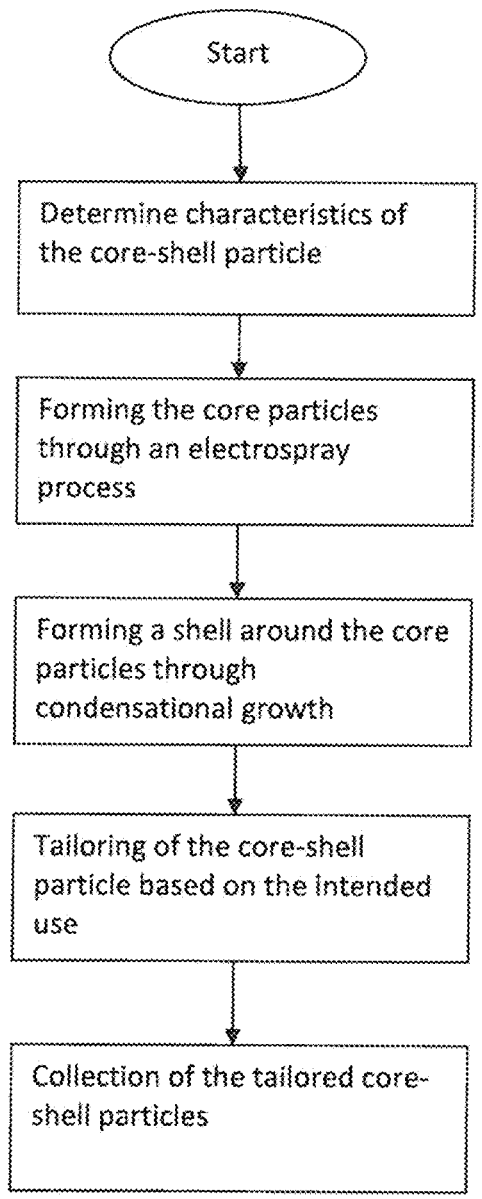

US011518691B2

(12) United States Patent
Zimmer

(10) Patent No.: US 11,518,691 B2
(45) **Date of Patent: *Dec. 6, 2022**

(54) HIGHLY TUNABLE FLUORESCENT CORE-SHELL PARTICLES FOR ENVIRONMENTAL RELEASE SIMULATION AND TRACKING APPLICATIONS

(71) Applicant: U.S. Environmental Protection Agency, Washington, DC (US)

(72) Inventor: Anthony Todd Zimmer, Cincinnati, OH (US)

(73) Assignee: U.S. Environmental Protection Agency, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/118,875

(22) Filed: Dec. 11, 2020

(65) Prior Publication Data

US 2022/0186111 A1 Jun. 16, 2022

Related U.S. Application Data

(62) Division of application No. 16/022,153, filed on Jun. 28, 2018, now Pat. No. 10,941,057.

(60) Provisional application No. 62/602,565, filed on Apr. 28, 2017.

(51) Int. Cl.

| | |
|---|---|
| *C02F 1/461* | (2006.01) |
| *C02F 1/48* | (2006.01) |
| *G01N 30/72* | (2006.01) |
| *G01N 31/22* | (2006.01) |
| *G01N 1/30* | (2006.01) |
| *C09K 11/02* | (2006.01) |
| *C09K 11/06* | (2006.01) |
| *G01N 15/06* | (2006.01) |
| *G01N 33/18* | (2006.01) |
| *C02F 101/30* | (2006.01) |
| *B82Y 30/00* | (2011.01) |

(52) U.S. Cl.

CPC ............ *C02F 1/46109* (2013.01); *C02F 1/48* (2013.01); *C09K 11/025* (2013.01); *C09K 11/06* (2013.01); *G01N 1/30* (2013.01); *G01N 15/06* (2013.01); *G01N 30/7266* (2013.01); *G01N 31/22* (2013.01); *G01N 33/18* (2013.01); *B82Y 30/00* (2013.01); *C02F 2001/46152* (2013.01); *C02F 2101/308* (2013.01); *C02F 2201/46135* (2013.01); *C02F 2201/46145* (2013.01); *C09K 2211/1007* (2013.01); *C09K 2211/1018* (2013.01); *G01N 2015/0693* (2013.01)

(58) Field of Classification Search

CPC .................. C09K 11/025; C09K 11/06; C09K 2211/1007; C09K 2211/1018

See application file for complete search history.

(56) References Cited

U.S. PATENT DOCUMENTS

| | | | | |
|---|---|---|---|---|
| 7,306,809 | B2 * | 12/2007 | Sojka | A61K 8/731 424/401 |
| 9,372,198 | B2 * | 6/2016 | Gonda | G01N 21/6486 |
| 2018/0312414 | A1 * | 11/2018 | Zimmer | G01N 30/7266 |

FOREIGN PATENT DOCUMENTS

| | | | |
|---|---|---|---|
| JP | 03-025892 | * | 2/1991 |

OTHER PUBLICATIONS

Translation for JP 03-025892, Feb. 4, 1991.*

* cited by examiner

*Primary Examiner* — C Melissa Koslow

(74) *Attorney, Agent, or Firm* — Jeffrey D. Moy; Weiss & Moy, PC

(57) ABSTRACT

A particle for emulating pollutant tracking in water has a florescent core. A semitransparent shell is formed around the florescent core.

9 Claims, 4 Drawing Sheets

FIG. 1

Floating bio/photodegradable particles
that act as a continuous oil slick

Neutrally buoyant/photodegradable particles
that act as discrete oil droplets

HIGHLY TUNABLE FLUORESCENT CORE-SHELL PARTICLES FOR ENVIRONMENTAL RELEASE SIMULATION AND TRACKING APPLICATIONS

RELATED APPLICATIONS

This patent application is related to U.S. Provisional Application No. 62/602,565 filed Apr. 28, 2017, entitled "Highly Tunable Fluorescent Core-Shell Particles for Environmental Release Simulation and Tracking Applications" and U.S. Pat. No. 10,941,057 B2, issued on Mar. 9, 2021 both in the name of the Anthony Todd Zimmer, and both of which are incorporated herein by reference in theft its entirety. The present patent application claims the benefit under 35 U.S.C. § 119(e).

TECHNICAL FIELD

The present application relates generally to the technical field of devices for studying environmental contaminants, and more specifically, to the technical field of tunable fluorescent core-shell particles having a uniform size for environmental release simulation and tracking applications.

BACKGROUND

Each year there are thousands of oil and/or chemical spills. Many of these oil and/or chemical spills occur in different waterways around the world. The release of oil and chemicals into these waterways is a major environmental problem. These spills may kill wildlife, destroy/damage the surrounding environment, and contaminate critical resources in the food chain. Spills may further pose economic damage to the effected communities by forcing the closure of fisheries, driving away tourists, or temporarily shutting down navigation routes. These environmental and economic damages can linger for years.

Because of the damage that may be caused by oil/chemical spills, it may be beneficial to forecast where a given spill might go and its potential effects on the waterway environment. A well-designed oil/chemical spill contingency plans can aid in spill response efforts. However, it is difficult to develop and/or optimize an effective contingency plan without using the actual chemical or an accurate simulant as the test media.

For oil spills, researchers have used a variety of different materials to track/emulate crude oil movement. Materials such as coffee beans, peat moss, cotton seed hulls, wood chips and similar materials have been used to track/emulate crude oil movement. Unfortunately, these materials do not adequately represent actual crude oil behavior as they poorly mimic surface behavior of the oil droplets. Further, the materials offer no understanding of the sub-surface transport of the oil droplet. Additionally, traditional tracers, such as florescent dyes used in water studies, are problematic as they rapidly dilute in water, have low absorption rates, and are readily degraded with sun exposure.

Therefore, it would be desirable to provide a system and method that overcomes the above. The system and method would provide a simulant/tracer material that more accurately mimics environmental contaminants.

SUMMARY

In accordance with one embodiment, a particle for emulating pollutant tracking in water is disclosed. The particle has a florescent core. A semitransparent shell is formed around the florescent core.

In accordance with one embodiment, a method of forming particles for emulating pollutant tracking in water is disclosed. The method comprises: forming florescent cores using electrospray generation; and forming semitransparent shells around the florescent cores by condensational growth.

In accordance with one embodiment, a method of forming particles for emulating pollutant tracking in water is disclosed. The method comprises: forming florescent cores using electrospray generation, wherein forming the florescent cores using electrospray generation comprises spraying a florescent dye through at least one spray nozzle into an electrospray chamber forming a plurality of monodisperse florescent cores; forming semitransparent shells around the florescent cores; and tailoring exterior surfaces of the particles to copy transport properties of the pollutant.

BRIEF DESCRIPTION OF THE DRAWINGS

The present application is further detailed with respect to the following drawings. These figures are not intended to limit the scope of the present application but rather illustrate certain attributes thereof. The same reference numbers will be used throughout the drawings to refer to the same or like parts.

Figure 1:
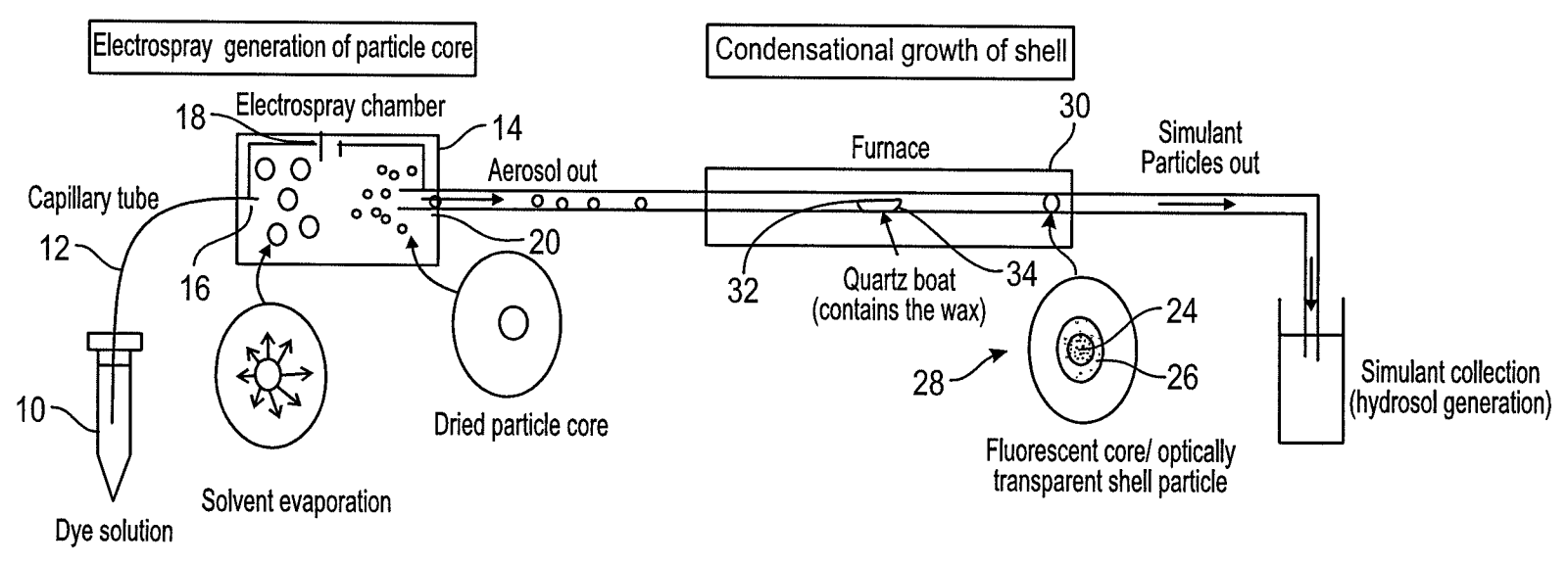

FIG. 1 is an exemplary embodiment of a block diagram for forming tunable core-shell particles for environmental release simulation and tracking applications in accordance with one embodiment of the present invention;

FIG. 2 is an exemplary flowchart showing a method for forming tunable core-shell particles for environmental release simulation and tracking applications in accordance with one embodiment of the present invention; and FIG. 3A-3C are exemplary embodiments of tunable core-shell particles for environmental release simulation and tracking applications in accordance with one embodiment of the present invention.

DESCRIPTION OF THE APPLICATION

The description set forth below in connection with the appended drawings is intended as a description of presently preferred embodiments of the disclosure and is not intended to represent the only forms in which the present disclosure can be constructed and/or utilized. The description sets forth the functions and the sequence of steps for constructing and operating the disclosure in connection with the illustrated embodiments. It is to be understood, however, that the same or equivalent functions and sequences can be accomplished by different embodiments that are also intended to be encompassed within the spirit and scope of this disclosure.

Embodiments of the exemplary system and method disclose tunable core-shell particles for environmental release simulation and tracking applications. The tunable core-shell particles may be tuned for specific environmental applications. The tunable core-shell particles may be designed to be readily detected in both concentrated and diluted conditions, environmentally degradable to minimize short and long-term effects to the environment and mimic as accurately as possible to the necessary transport properties of the environmental contaminate.

Referring to FIGS. 1-2, a process for forming tunable core-shell particles for environmental release simulation and tracking applications may be shown. The process is a multi-step process wherein a core particle may be first formed. Once the core particle is formed, a shell may be formed around the core particle thereby forming the core-shell particles.

The core-shell particles may be tuned for specific environmental applications. Thus, the characteristics of the core-shell particles should first be determined. Based on the characteristics of the core-shell particles, the core-shell particles may be produced.

As disclosed above, the core particle may first be formed. In accordance with one embodiment, the core particle may be formed through an electrospraying process. Electrospraying is a method of liquid atomisation by electrical forces. A high voltage electric field may be used to break up a solution 10. The high voltage electric field may produce core particles that are highly charged thereby preventing coagulation and promoting self-dispersion.

Electrospraying may allow one to control the size of the core particle being produced. The size of the core particle may range from micro- to nano-sized core particles. The core particle size may be controlled by varying the solution properties such as concentration and conductivity, as well as processing parameters such as flow rate and applied voltage.

A solution 10 may form the contents of the core. The type of solution used may be based on the specific environmental application. In accordance with one embodiment, the solution 10 may be a dye solution. The dye solution may be a florescent dye solution such as rhodamine, fluorescein, and p-toluenesulfonic acid (PTSA), as well as other custom dye blends that may have unique properties that are beneficial to a specific environment or study. As disclosed above, the type of dye solution may be tailor the selection of the solution 10 to meet the environmental application requirements. For example, selecting fluorescein as an oil simulant in an open water response exercise would allow responders to clearly see the simulant without being masked by other interfering materials in the water such as human/plant organics.

The solution 10 may be fed into an electrospray chamber 14 via a capillary tube 12. Within the electrospray chamber, the solution 10 flows through an emitter 16 formed at the end of the capillary tube 12. A power supply 18 forms a high voltage which is applied at the tip of the emitter 16 and an electrical field is formed with a grounded collector 20. When the energy of the electric field overcomes the surface tension of the solution 10, the solution 10 breaks into small charged particles. The charged particles evaporate as they travel towards the mass spectrometer inlet 22 to produce a dried core particle 24.

Electrospraying may allow for efficient, high production volumes of the core particle 24. Several advantages of this process include continuous operation as well as inherent scalability (e.g., using 100 spray nozzles instead of one). Electrospraying further allows for production of highly monodisperse core particles 24. This process uses electrosprays that are desired for their inherent ability to produce uniform core particle sizes. Uniform (i.e., monodisperse) core particles 24 provide very tight control in tailoring the synthesis process for the desired environmental application.

As disclosed above, the size of the core particle 24 may be controlled by varying the solution properties such as concentration and conductivity, as well as processing parameters such as flow rate and applied voltage. Production of core particles 24 can be specifically tuned to produce particle sizes ranging from nanometer to micrometer particle sizes. As an example, nanometer-scaled core particles 24 could be produced whose quantum light emissions are significantly higher than that predicted by individual molecules. In other words, this process could produce environmentally benign "quantum dots" that could be used as a tracer having detection limits <1 part per billion concentrations.

Once the core particles 24 is generated, a shell 26 may be formed around the core particle 24 to form the core-shell particle 28. In accordance with one embodiment, the shell 26 may be semitransparent/transparent. This may allow one to see the florescent nature of the core particle 24.

Different semitransparent/transparent materials may be used to form the shell 26. In accordance with one embodiment, naturally occurring materials such as animal/plant wax may be used as these materials may be biodegradable and may be less harmful to the environment.

The shell 26 may be formed by various processes. In the embodiment shown in FIGS. 1-2, the shell 26 may be formed by a condensational growth process. Once the core particles 24 are formed, the core particles 24 may be sent to a furnace 30. The core particles 24 may be placed in a holder 32. The holder 32 may contain a compound 34 for forming the shell 26. The heat of the furnace 30 may cause the compound 34 to form a vapor air mixture coating the core particle 24 to form the shell 26. In the present embodiment, the holder 32 may be a quartz boat. The quartz boat may be use as it is able to retain heat for longer periods of time.

As disclosed above, the material used to form the shell 26 may be tailored to meet the environmental detection requirements. For example, a thick carnauba plant wax (specific gravity less than water) could be used to form the shell 26. The carnauba plant wax may serve their environmental detection purpose and will naturally degrade in the environment (e.g., biodegradation of shell by wax-degrading bacteria). Further, since the carnauba plant wax has a specific gravity less than water, the shell 26 and hence the core-shell particle 28 should be able to float on the water surface. If fluorescein is used to form the core particles 24, the core particles 24 should naturally degrade by photolysis of the fluorescein through sun exposure.

In the above embodiment, the carnauba plant wax may be placed in the holder 32 with the core particle 24. The heat of the furnace 30 may cause the carnauba plant wax forming the compound 34 to form a carnauba wax vapor/air mixture coating the core particle 24 to form the shell 26 and hence the core-shell particle 28.

The core-shell particles 28 may then exit the furnace 30. The core-shell particles 28 may be tailored based on the intended use. For example, the core-shell particles 28 may be functionalized to produce desired particle-particle and particle-media (e.g., soil) behavior. As an example, the surface of the core-shell particles 28 could be charged such that the core-shell particles 28 do not agglomerate and behave as single, discrete particles. Once the core-shell particles 28 may be tailored based on the intended use, the tailored core-shell particles 28 may be collected and stored.

Figure 3A:
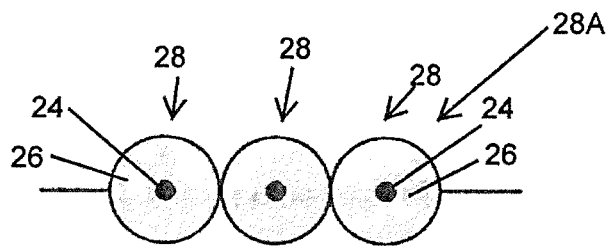
Figure 3B:
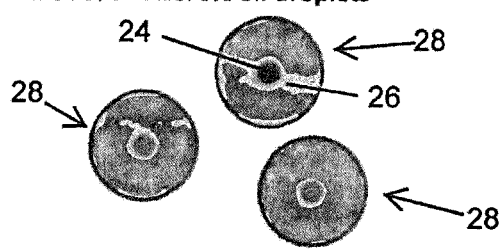
Figure 3C:
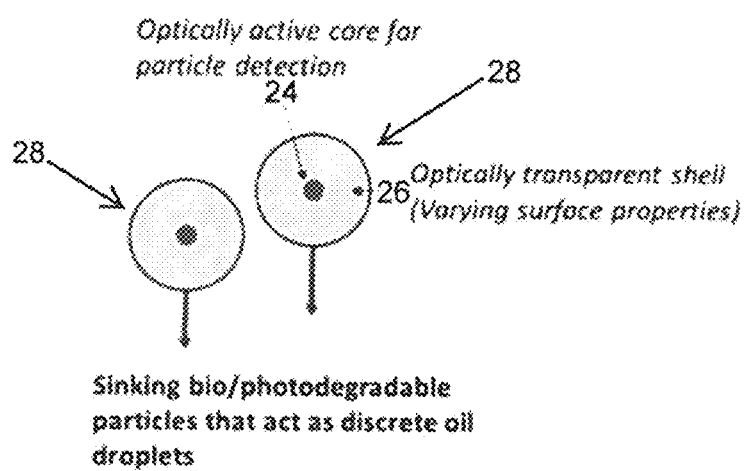

The core-shell particles 28 may be functionalized based on the core-shell particles 28 intended purpose. Referring to FIGS. 3A-3C, different embodiments of the core-shell particles 28 may be seen. In FIG. 3A, the core-shell particles 28 may be tuned to have a florescent core particle 24 and float. The core-shell particles 28 may have a tunable surface to promote adhesion so that the core-shell particles 28 stick together to form a cohesive unit 28A. The cohesive unit 28A may be used to mimic an oil stick. The core-shell particles 28 may be formed so that the core particle 24 and shell 26 are biodegradable and/or naturally degrade by photolysis.

In FIG. 3B, the core-shell particles 28 may be tuned to have a florescent core particle 24 and float. In this embodiment, the core-shell particles 28 may have a tunable surface so that the core-shell particles 28 repel one another to mimic individual oil droplets. The core-shell particles 28 may be formed so that the core particle 24 and shell 26 are biodegradable and/or naturally degrade by photolysis.

In FIG. 3C, the core-shell particles 28 may be tuned to have an optically active florescent core particle 24 for particle detection. The core-shell particles 28 may be designed to sink. In this embodiment, the core-shell particles 28 may have a tunable surface so that the core-shell particles 28 repel one another to mimic individual oil droplets. The core-shell particles 28 may be formed so that the core particle 24 and shell 26 are biodegradable and/or naturally degrade by photolysis.

The core-shell particles 28 provides may benefits over current materials used to track/emulate crude oil/chemical movement. The core-shell particles 28 can be engineered both as a simulant (e.g., oil droplets) and tracer (e.g., forensic tracking of an environmental contaminant). Environmental media applications range from open water (e.g., oceans, rivers) to complex environmental media (e.g., soils/sediments) transport. The core-shell particles 28 may be tunable to form a particular size/density/surface behavior to mimic the transport environmental contaminants (e.g., oil simulant for emergency response). The core-shell particles 28 may be formed with physical diameters ranging from nanometers to micrometers. The core-shell particles 28 may have a tunable surface to promote a variety of desired behaviors (e.g., stick together to mimic an oil stick or repeal one another or environmental media such as a soil).

The foregoing description is illustrative of particular embodiments of the application but is not meant to be a limitation upon the practice thereof. The following claims, including all equivalents thereof, are intended to define the scope of the application.

What is claimed is:

1. A particle for emulating pollutant tracking in water comprising:
   a florescent core; and
   a semitransparent shell formed around the florescent core, wherein the semitransparent shell is charged to one which attracts or repels adjacent particles for emulating pollutant tracking.

2. The particle of claim 1, wherein the florescent core and semitransparent shell are biodegradable.

3. The particle of claim 1, wherein the semitransparent shell is formed of one of a plant or animal wax.

4. The particle of claim 1, wherein the florescent core is formed of one of rhodamine, fluorescein, or p-toluene sulfonic acid (PTSA).

5. The particle of claim 1, wherein the florescent core is formed through electrospray generation.

6. A particle for emulating pollutant tracking in water comprising:
   a florescent core, wherein the florescent core is formed by spraying a florescent dye;
   and a semitransparent shell formed around the florescent cores by applying a vapor/air mixture to coat the florescent cores, the semitransparent shells being biodegradable, wherein the semitransparent shell is charged to one which attaches or repels adjacent particles for emulating pollutant tracking.

7. The particle of claim 6, wherein the semitransparent shell is charged to attach to adjacent particles.

8. The particle of claim 6, wherein the semitransparent shell is charged to repeal adjacent particles.

9. The particle of claim 6, wherein the florescent dye is one of rhodamine, fluorescein, or p-toluene sulfonic acid (PTSA).

* * * * *